(12) United States Patent
Araki et al.

(10) Patent No.: US 7,579,325 B2
(45) Date of Patent: Aug. 25, 2009

(54) DRUGS CONTAINING REDUCED OF VITAMIN $B_2$

(75) Inventors: Seiichi Araki, Ibaraki-ken (JP); Mamoru Suzuki, Ibaraki-ken (JP); Yoshiki Sugihara, Ibaraki-ken (JP); Toshio Toyosawa, Ibaraki-ken (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 661 days.

(21) Appl. No.: 10/472,621

(22) PCT Filed: Mar. 19, 2002

(86) PCT No.: PCT/JP02/02616

§ 371 (c)(1),
(2), (4) Date: Sep. 19, 2003

(87) PCT Pub. No.: WO02/074313

PCT Pub. Date: Sep. 26, 2002

(65) Prior Publication Data

US 2004/0106562 A1    Jun. 3, 2004

(30) Foreign Application Priority Data

Mar. 21, 2001  (JP) ............................. 2001-080578

(51) Int. Cl.
*A61K 31/70* (2006.01)
*A61K 31/495* (2006.01)
*A61K 31/675* (2006.01)

(52) U.S. Cl. ........................ 514/43; 514/250; 514/81
(58) Field of Classification Search .................. 514/43, 514/250, 81
See application file for complete search history.

(56) References Cited

U.S. PATENT DOCUMENTS

| 2,970,995 | A | * | 2/1961 | Wheeler | 544/251 |
| 4,956,381 | A | | 9/1990 | Bollinger et al. | 514/443 |
| 5,334,510 | A | | 8/1994 | Usui et al. | 435/66 |
| 5,714,469 | A | * | 2/1998 | DeMarsh | 514/15 |
| 5,814,632 | A | | 9/1998 | Araki et al. | 514/251 |
| 5,945,420 | A | | 8/1999 | Araki et al. | 514/251 |
| 2003/0143265 | A1 | | 7/2003 | Araki et al. | |
| 2003/0161871 | A1 | | 8/2003 | Hird et al. | |
| 2003/0162751 | A1 | | 8/2003 | Grobin et al. | |

FOREIGN PATENT DOCUMENTS

| DE | 4328871 A1 | * | 3/1995 |
| EP | 319463 A2 | | 6/1989 |
| EP | 319463 A3 | | 6/1989 |
| EP | 531708 A2 | | 3/1993 |
| EP | 578733 A1 | | 1/1994 |
| EP | 679398 A1 | | 11/1995 |
| JP | 1-146819 | | 6/1989 |
| JP | 5-64597 | | 3/1993 |
| JP | 5-201864 | | 8/1993 |
| JP | 6-506212 | | 7/1994 |
| JP | 9-301861 | | 11/1997 |
| JP | 10-29941 | | 2/1998 |
| JP | 11-199486 | | 7/1999 |
| JP | 11-199513 | | 7/1999 |
| JP | 2000-80046 | | 3/2000 |
| JP | 2000-178246 | | 6/2000 |
| JP | 2000-297046 | | 10/2000 |
| JP | 2000-297049 | | 10/2000 |
| JP | 2000-302768 | | 10/2000 |
| WO | WO 92/17173 A2 | | 10/1992 |
| WO | WO 93/05784 A1 | | 4/1993 |
| WO | WO 95/22898 | | 2/1995 |
| WO | WO 95/05852 | | 3/1995 |
| WO | WO 97/36594 A1 | | 10/1997 |
| WO | WO 02/03972 | | 1/2002 |

OTHER PUBLICATIONS

Lahnborg et al. Efficacy of tinidazole compared to clindamycin in the treatment of experimentally induced intra-abdominal sepsis. The Birtish socciety for Antimicrobial Chemotherapy. 1982; 10 (suppl. a); pp. 117-121.*
U.S. Appl. No. 10/145,006, filed May 14, 2002, Hird et al.
Akompong T. et al., "In Vitro Activity of Riboflavin against the Human Malaria Parasite *Plasmodium falciparum*", *Antimicrobial Agents and Chemotherapy*, 2000, 44(1), 88-96.
International Search Report issued for corresponding PCT application PCT/JP02/02616 (WO 02/074313). 2002.
Liu et al. "Effect of NADH on Immunological Cells in the Peripheral Blood After Radiation" *Mianyixue Zazhi Bianjibu* (2001) 17:444-445 and 448 (Chemical Abstract).
Xu and Hultquist, "Coupling of Dihydroriboflavin Oxidation to the Formation of the Higher Valence States of Hemeproteins," *Biochemical and Biophysical Research Communications* (1991) 181:197-203.

* cited by examiner

*Primary Examiner*—Jennifer Myong M Kim
(74) *Attorney, Agent, or Firm*—Andrea L. C. Robidoux; Choate Hall & Stewart, LLP

(57) ABSTRACT

The present invention provides medicines for preventing or treating infectious diseases, sepsis and/or septic shock, which exhibit excellent immunostimulating effects. More specifically, the invention provides medicines for immunostimulation and infection-protection and -treatment, and/or for preventing or treating sepsis and septic shock, which comprise reduced riboflavin and/or reduced riboflavin derivative or pharmacologically acceptable salt thereof. Also provided are methods for using them in the prevention and/or treatment of infectious disorders such as sepsis and septic shock.

2 Claims, No Drawings

DRUGS CONTAINING REDUCED OF VITAMIN B$_2$

PRIORITY INFORMATION

The present application claims the benefit under 35 U.S.C. § 371 of International Application No.: PCT/JP02/02616 (published PCT application No. WO 02/074313), filed 19 Mar. 2002, which claims priority to Japanese Patent Application No.: 2001-80578, filed 21 Mar. 2001, the entire contents of each of these applications are hereby incorporated herein by reference.

BACKGROUND OF THE INVENTION

Antibiotics such as anti-bacterial agents and anti-fungal agents are traditionally known to be effective for preventing or treating various infectious diseases and are widely used for clinical applications today. These antibiotics can be obtained by the extraction of products from bacteria or fungi or by chemical synthesis. However, when antibiotics of the same line are used repeatedly for a long period, the target bacteria may acquire resistance against the antibiotics and the effect of the antibiotics may not be developed anymore. This emergence of so-called resistant bacteria has become a serious social problem.

Thus, alternative approaches for protecting hosts via routes different from those of antibiotics have been considered. One representative example involves the potentiation of the immune functions of a host to protect the host from microbial infections. Examples of drugs useful for this approach include immunopotentiators/infection defense medicines and medicines for treating infections comprising riboflavin, which is known widely as vitamin B$_2$, or riboflavin derivatives such as riboflavin mononucleotides, and flavinadenine dinucleotides as described in the gazette of Japanese Kokai Publication Hei-5-201864 or corresponding U.S. Pat. Nos. 5,814,632 and 5,945,420.

Ascorbic acid, known as vitamin C, is also known to have the similar effect. It is described in JP-A 9-301861 that ascorbic acid derivatives are effective on bacterial shocks.

Furthermore, the gazette of Japanese Kokai Publication 2000-297046 discloses that an extract from sweet potato has an effect of stimulating immune of a living body and of preventing infections.

A systemic inflammatory reaction against infections, namely sepsis; i.e., systemic inflammatory response syndrome (SIRS), is a state where a microorganism such as a bacterium or a fungus developed in an infected host is proliferated in a large quantity in the living body and the cells of the microorganism or a metabolite thereof is transferred to the blood and circulated through the body. As this state is progresses, an exotoxin excreted from the microorganism cells or an endotoxin released upon the disruption of the microorganism cells, or a component constituting the microorganism cells is transferred to organs of the host. In the initial stage, fever, malaise and chill occur. As the condition progresses, multiple organ failure develops and symptoms such as impaired consciousness, dyspnea or decreased blood pressure occur, causing a state of shock often followed by death.

Consequently, potent antibiotics are administered to kill microorganisms in the infected host in the initial stage of sepsis, and systemic management such as reinfusion or artificial respiration is applied and simultaneously hemodialysis, plasma exchange or administration of a drug (catecholamine) is performed in the advanced stages. However, the efficacy of these approaches is not always satisfactory.

Recently, medicines for preventing or treating toxin shocks comprising vitamin B$_2$ have been reported in the gazette of Japanese Kokai Publication Hei-10-29941. In addition, the gazette of Japanese Kokai Publication 2000-178246 discloses cycloalkene derivatives for use in the treatment of septic shock; the gazette of Japanese Kokai Publication 2000-80046 discloses medicines for preventing or treating syndromes that develop in the exacerbated state of sepsis; and the gazette of Japanese Kokai Publication 2000-302768 discloses hydrazone derivatives for use in the treatment of endotoxin shock. Furthermore, the gazettes of Japanese Kokai Publication Hei-5-201864 and of Japanese Kokai Publication Hei-10-29941 disclose medicines for immunostimulation and infection-protection and -treatment comprising riboflavin and/or a riboflavin derivative as active ingredient and medicines for preventing or treating toxin shocks, respectively. However, no description about reduced riboflavin is found in these patent publications.

Turning to infections from the malaria protozoa, Japanese patent publication No. Hei-6-506212 discloses that riboflavin is effective for the prevention and treatment of malarian diseases. Furthermore, Antimicrobial Agents and Chemotherapy 44(1), 88-96, 2000, reports that "malaria parasite proliferates by digesting hemoglobin in erythrocytes and oxidizing the hemoglobin to convert it to methemoglobin. Since riboflavin is able to reduce methemoglobin to hemoglobin, the treatment with riboflavin reduced the amount of hemoglobin in the body of malaria parasite, resulting in inhibition of proliferation of malaria parasite."

However, the medicines for immunostimulation and infection-protection and -treatment, the medicines for preventing or treating sepsis and the medicines for preventing or treating septic shock as mentioned above are not always effective on all patients or animals and the efficacy of these medicines is not also satisfactory. Therefore, the development of medicines for immunostimulation and infection-protection and -treatment, and for preventing or treating sepsis and septic shock with better efficacy is desired.

DETAILED DESCRIPTION OF CERTAIN PREFERRED EMBODIMENTS OF THE INVENTION

The inventors have completed thorough research in light of such circumstances, the results of which have unexpectedly revealed that reduced vitamin B$_2$ has a more potent immunoregulating effect than aforementioned vitamin B$_2$, which culminated in the present invention. Specifically, reduced vitamin B$_2$ has been found to allow a living body to maintain homeostasis by stimulating the immune system when the immune function of the living body is reduced by infections or the like, or by inhibiting excess immunostimulation such as shocks and inflammatory reactions when such reactions are found in the living body.

The present invention also relates to medicines for immunostimulation and infection-protection and -treatment, and/or medicines for preventing or treating sepsis, which comprise reduced vitamin B$_2$ (i.e., reduced riboflavin) and/or a reduced riboflavin derivative or pharmacologically acceptable salts thereof as active ingredient. Medicines for preventing or treating sepsis may be medicines for preventing or treating septic shock, disseminate intravascular coagulation (DIC), multiple organ failure (MOF) and/or adult respiratory distress syndrome (ARDS). The medicines may also be for preventing or treating toxin shock as the septic shock.

The present invention provides a method for immunostimulation and infection-protection, or for preventing or treating sepsis, septic shock or malaria, which comprises administering a pharmacologically effective amount of reduced riboflavin and/or a reduced riboflavin derivative or a pharmacologically acceptable salt thereof to a subject.

The present invention also provides use of reduced riboflavin and/or reduced riboflavin derivatives or pharmacologically acceptable salts thereof for the production of medicines for immunostimulation and infection-protection and -treatment, and/or medicines for preventing or treating sepsis, septic shock or malaria.

The present inventors have found that, among riboflavin derivatives, particularly reduced forms thereof have remarkably strong immunostimulating and infection-protective/curative effects, sepsis-preventive/curative effects and septic shock-preventive/curative effects and/or toxin shock-preventive/curative effects, which culminated in the present invention.

The present invention also provides medicines for preventing or treating malarian diseases comprising reduced riboflavin and/or a reduced riboflavin derivative or a pharmacologically acceptable salt thereof as active ingredient. Since reduced forms of riboflavin and/or riboflavin derivatives, or pharmacologically acceptable salts thereof have a higher reductive effect than riboflavin and/or riboflavin derivatives or pharmacologically acceptable salts thereof, it is proposed that they can inhibit the growth of malaria parasites more effectively.

Medicines for immunostimulation and infection-protection or -treatment, for preventing or treating sepsis, for preventing or treating septic shock and/or for preventing or treating malaria according to the present invention include the cases where a precursor of reduced riboflavin and/or a reduced riboflavin derivative or pharmacologically acceptable salt thereof (e.g., riboflavin and/or a riboflavin derivative or pharmacologically acceptable salt thereof) administered to a subject may be converted (e.g., reduced) in vivo to reduced riboflavin and/or a reduced riboflavin derivative or pharmacologically acceptable salt thereof, which exhibits an immunostimulating and infection-protective/curative effect, a septic shock-preventive/curative effect or a malaria-protective/curative effect in the subject.

Reduced riboflavin and/or reduced riboflavin derivatives or pharmacologically acceptable salts thereof according to the present invention refers to a reduced form of vitamin $B_2$ and is not particularly limited. Preferably the term encompasses reduced forms of riboflavin, flavin mononucleotide (riboflavin phosphate), flavin adenine dinucleotide and riboflavin tetrabutylate, and pharmacologically acceptable salts thereof. Reduced riboflavin may be, for example, leucoflavin or monohydroflavin or pharmacologically acceptable salts thereof. Reduced riboflavin derivatives may be, for example, leucoflavin mononucleotide (FMN-$H_2$), leucoflavin adenine dinucleotide (FAD-$H_2$) or pharmacologically acceptable salts thereof. The present invention encompasses pharmacologically acceptable salts, hydrates and the like of reduced riboflavin.

Reduced riboflavin and/or reduced riboflavin derivatives or pharmacologically acceptable salts thereof according to the present invention can be produced readily by the addition of a conventional reducing agent such as a hydrosulfite or tin chloride. For example, they can be produced by the method described in the Japanese Pharmacopoeia, $12^{th}$ revision (Hirokawa-Shoten, 1991), C-2278 (the article of "riboflavin"), "riboflavin can be reduced by reduction or catalytic reduction with a hydrosulfite or tin chloride to a leuco-type dihydroflavin (also referred to as "leucoflavin") through a semiquinone-type monohydroflavin". For example, 120 mg of riboflavin sodium phosphate (FMN-Na) can be dissolved in 400 ml of physiological saline and then mixed with 4.8 g of sodium hydrosulfite to produce leucoflavin sodium phosphate (FMN-Na-$H_2$). Of course, the method for producing reduced riboflavin and/or reduced riboflavin derivatives or pharmacologically acceptable salts thereof of the present invention is not limited to this method.

Riboflavin, a monohydroflavin and a dihydroflavin (leucoflavin) can be produced mutually by a oxidation/reduction reversible reaction. Riboflavin and/or riboflavin derivatives or pharmacologically acceptable salts thereof are surmised to be converted into reduced riboflavin and/or reduced riboflavin derivatives or pharmacologically acceptable salts thereof via in vivo reduction. Therefore, in medical applications of reduced riboflavin and/or reduced riboflavin derivatives or pharmacologically acceptable salts thereof according to the present invention, riboflavin and/or a riboflavin derivative or pharmacologically acceptable salt thereof (e.g., riboflavin sodium phosphate) may be administered to a subject to induce the production of reduced riboflavin and/or a reduced riboflavin derivative or pharmacologically acceptable salt thereof (e.g., leucoflavin sodium phosphate, monohydroflavin sodium phosphate) in the patient subject via in vivo metabolism, which exhibits the pharmacological activities of the present invention. This case is also encompassed in the present invention.

Accordingly, the present invention provides a method for the prevention and treatment of a target disease described in the present invention, which comprises administering riboflavin and/or a riboflavin derivative or pharmacologically acceptable salt thereof to produce reduced riboflavin and/or a reduced riboflavin derivative or a pharmacologically acceptable salt in vivo. Preferably, the present invention provides a method for the prevention and treatment of a target disease described in the present invention, which comprises administering riboflavin sodium phosphate to produce leucoflavin sodium phosphate and/or monohydroflavin sodium phosphate in vivo.

The present invention also provides a method for immunostimulation and infection-protection, or preventing or treating sepsis, septic shock or malaria by the action of reduced riboflavin and/or a reduced riboflavin derivative or pharmacologically acceptable salt thereof which is produced in vivo, which comprises administering a pharmacologically effective amount of riboflavin and/or a riboflavin derivative or pharmacologically acceptable salt thereof to a subject.

The present invention also provides medicines for immunostimulation and infection-protection and -treatment, and/or for preventing or treating sepsis, septic shock or malaria comprising, as active ingredient, reduced riboflavin and/or a reduced riboflavin derivative or pharmacologically acceptable salt thereof which is produced in vivo by administering riboflavin and/or a riboflavin derivative or pharmacologically acceptable salt thereof.

The present invention also provides use of riboflavin and/or a riboflavin derivative or pharmacologically acceptable salt thereof for the production of medicines for immunostimulation and infection-protection, or for preventing or treating sepsis, septic shock or malaria by the action of reduced riboflavin and/or a reduced riboflavin derivative or pharmacologically acceptable salt thereof which is produced in vivo by administering riboflavin and/or a riboflavin derivative or pharmacologically acceptable salt thereof.

Subjects to be administered with medicines of the present invention include humans and animals.

The term "animal" as used herein refers to an industrial animal, a companion animal or a laboratory animal. The industrial animal is an animal whose breeding is required for industrial purposes, including livestock animals such as cattle, horse, pig, goat or sheep; farm fowls such as chicken, duck, quail, turkey or ostrich; fishes such as yellowtail, young yellowtail, red sea beam, horse mackerel, carp, rainbow trout or eel. The companion animal refers to a so-called pet, including dog, cat, marmoset, small birds, hamster and gold fish. The laboratory animal refers to an animal used for studies in the fields of medicine, biology, agriculture, pharmacy and the like, including rat, guinea pig, beagle, miniature pig, rhesus monkey and cynomolgus monkey.

For the administration to a human or animal which has not been infected yet, which has not developed sepsis, septic shock or toxic shock, or which has been recovered from any one of these diseases, the medicine may be used as a preventive medicine. For the administration to a human or animal after infection or during the development of any one of these diseases, the medicine may be used as a therapeutic medicine.

The term "sepsis" as used herein refers to a state where microbial infection is developed systemically, or a state where a subject is infected with a microorganism topically or systemically and an exotoxin excreted from the microorganism, an endotoxin excreted upon the disruption of the microorganism or a component constituting the microorganism is spread systemically.

The term "septic shock" as used herein refers to a state where dysfunction of at least one organ (e.g., heart, lung, liver, kidney, spleen, brain and spinal cord) occurs as the result of the systemic spread of the above-mentioned exotoxin, endotoxin or the microorganism-constituting component, or a state where a symptom such as weakness, vertigo, dysstasia, decreased blood pressure, fall of body temperature, arrhythmia, ventricular fibrillation, dyspnea, fall of body temperature, convulsions, clouding of consciousness and unconsciousness occurs as the result of the dysfunction of the organs.

Medicines according to the present invention may be administered by any route depending on the purposes of the administration, symptoms or the like, and may be administered by an intravenous, intramuscular, intraperitoneal, subcutaneous, transdermal or oral route, or in the form of an eye drop. Preferably, the medicines are administered intravenously, intramuscularly or subcutaneously, particularly preferably intravenously.

The dosage may vary depending on the purposes of administration, types of the diseases to be treated and state of the symptoms. For intravenous administration, the dosage may be 0.1 to 50 mg/kg, preferably 0.3 to 20 mg/kg, more preferably 0.3 to 2 mg/kg. For intramuscular administration, the dosage may be 0.1 to 50 mg/kg, preferably 3 to 20 mg/kg. For oral administration, the dosage may be 1 to 100 mg/kg, preferably 10 to 500 mg/kg, more preferably 30 to 200 mg/kg.

Medicines according to the present invention may be administered without being processed or in the form of an injection solution (for intravenous, intramuscular, subcutaneous or intraperitoneal administration), an oral preparation (tablets, granules, powder, capsules), a transdermal preparation or an eye drop which may be prepared by mixing with any conventional pharmaceutical additives in a conventional manner. The medicine may also be blended in a food, a feed, drink water or the like.

Injectable preparations may be prepared by conventional methods, by adding, as needed, pH adjusting agents, buffering agents, emulsifying agents, solubilizers, antioxidants, preservatives, isotonic agents or the like to reduced riboflavin and/or reduced riboflavin derivatives, or pharmacologically acceptable salts thereof. The injectable preparation may be freeze-dried to produce a lyophilized preparation of the extemporaneous type (i.e., the type of dissolving at the time of use). These injectable preparations may be administered intravenously, subcutaneously, intramuscularly or the like.

pH Adjusting agents and buffering agents include organic or inorganic acids and/or a salts thereof, sodium hydroxide and meglumine. Emulsifying agents include methylcellulose, polysorbate 80, hydroxyethylcellulose, gum arabica, sodium carboxymethylcellulose and polyoxyethylene sorbitan monolaurate. Solubilizers include polyoxyethylene hydrogenated castor oil, polysorbate 80, nicotinic acid amide and polyoxyethylene sorbitan monolaurate. Antioxidants include ascorbic acid, α-tocopherol, ethoxyquin, dibutyl hydroxytoluene and dibutyl hydroxyanisole. Preservatives include methyl paraoxybenzoate, ethyl paraoxybenzoate and sorbic acid. However, they are not limited thereto.

Oral solid preparations may be prepared in the form of tablets, coated tablets, granules, powder or capsules by conventional methods, by adding as needed excipients, binders, disintegrating agents, lubricants, coloring agents, flavoring agents, anti-oxidants, solubilizing agents or the like to reduced riboflavin and/or reduced riboflavin derivatives, or pharmacologically acceptable salts thereof.

Excipients include, but are not limited to, starch, corn starch, dextrin, glucose, lactose, saccharose, sugar alcohol, hydrogenated oil, mannitol, microcrystalline cellulose, anhydrous silicon, calcium silicate and dibasic calcium phosphate. Binders include, but are not limited to, polyvinyl pyrrolidone, ethylcellulose, methylcellulose, gum arabic, hydroxypropylcellulose, hydroxypropylmethylcellulose, sodium carboxymethylcellulose, propylene glycol and poly(sodium acrylate). Lubricants include, but are not limited to, magnesium stearate, talc and calcium stearate. Antioxidants include, but are not limited to, ascorbic acid, α-tocopherol, ethoxyquin, dibutyl hydroxytoluene and dibutyl hydroxyanisole. A coloring agent, a flavoring agent and the like may be added. In tablets, granules and powder, a film coating may be applied, if needed.

Species of the infection-causing microorganism against which administration of the inventive medicines for immunostimulation and infection-protection and -treatment, for preventing of treating sepsis, for preventing or treating septic shock or for preventing or treating toxin shock of the present invention comprising reduced riboflavin and/or a reduced riboflavin derivative or pharmacologically acceptable salt thereof may be effective are not particularly limited. In general, the microorganisms include bacteria, fungi, parasites or protozoa, viruses, mycoplasmas, rickettsias and chlamydias. Particularly, it is found that the medicines of the present invention may be highly effective against bacteria, fungi and parasites or protozoa.

Bacteria against which medicines of the present invention may act effectively include, for example, *Escherichia coli* including various pathogenic coliforms; bacteria belonging to the genus *Salmonella* such as *Salmonella typhimurium, S. typhi, S. paratyphi, S. enteritidis, S. cholerasuis, S. gallinarum, S. abortasequi, S. abortasovis* or *S. dublin*; bacteria belonging to the genus *Shigella* such as *Shigella sonnei, S. dysenteriae, S. flexneri* or *S. boydii*; bacteria belonging to the genus *Yersinia* such as *Yersinia pestis, Y. pseudotuberculosis* or *Y. enterocolitica*; bacteria belonging to the genus *Citrobacter* such as *Citrobacter freundii*; bacteria belonging the genus *Haemophilus* such as *Haemophilus somunus* or *H. parasuis*; bacterial belonging to the genus *Actinobacillus* such as *Actinobacillus lignieresii*; bacteria belonging to the genus *Pseudomonas* such as *Pseudomonas aeruginosa, P. mallei* or *P. fluorescens*; bacteria belonging to the genus *Bordetella* such as *Bordetella bronchiseptica* or *B. pertussis*; bacteria belonging to the genus *Brucella* such as *Brucella abortus, B. melitensis* or *B. canis; Neisseria meningitidis, N. gonorrhoeae*; bacteria belonging to the genus *Bacterodes*; bacteria belonging to the genus *Fusobacterium*; bacteria belonging to the genus *Veillonella*; bacteria belonging to the genus *Campylobacter* such as *Campylobacter fetus, C. sputorum, C. feacalis* or *C. jejuni*; bacteria belonging to the genus *Treponema*; bacteria belonging to the genus *Borrelia*; bacteria belonging to the genus *Spirichaeta*; bacteria belonging to the genus *Leptospira*; bacteria belonging to the genus *Staphylococcus* such as *Staphylococcus aureus* or *S. epidermidis*; bacteria belonging to the genus *Streptococcus* such as *Streptococcus pyogens, S. pneumoniae* or *S. mutanns*; bacteria belonging to the genus *Enterococcus* such as *Enterococcus faecalis*; bacteria belonging to the genus *Lactococcus* such as *Lactococcus garvidae*; bacteria belonging to the genus *Bacillus* such as *Bacillus anthracis* or *B. cereus*; bacteria belonging to the genus *Clostridium* such as *Clostridium perfingens, C. chauvoei, C. botulinum, C. tetani* or *C. septicum*; bacteria belonging to the genus *Listeria* such as *Listeria monocytogenes*; bacteria belonging to the genus *Erysipelothrix* such as *Erysipelothrix rhusiopathiae*; bacteria belonging to the genus *Corynebacterium* such as *Corynebacterium renale, C. cystitidis, C. pseudotuberculosis* or *C. diphtheriae*; bacteria belonging to the genus *Mycobacterium* such as *Mycobacterium tuberculosis, M. bovis, M. kansasii, M. ulcerance, M. goldnae, M. intracellulae, M. avium* or *M. leprae*; bacteria belonging to the genus *Actinomyces*; bacteria belonging to the genus *Serratia* such as *Serratia marcescens* or *S. rubidaea*; bacteria belonging to the genus *Vibrio* such as *Vibrio cholerae* or *V. parahaemolyticus*; bacteria belonging to the genus *Pasteurella* such as *Pasteurella multocida* or *P. haemolytica*; bacteria belonging to the genus *Enterobactor* such as *Enterobactor cloacae*; bacteria belonging to the genus *Citrobacter* such as *Citrobacter freundii*; bacteria belonging to the genus *Enterococcus* such as *Enterococcus seriolicida* (including macrolide-resistant bacteria); and bacteria belonging to the genus *Proteus*. However, the present invention is not intended to be limited by the species of the bacteria.

The present invention may also be effective against various resistant bacteria such as methicillin-resistant *Staphylococcus aureus* (MRSA) or penicillin-resistant *Streptococcus pneumoniae* (PRSP).

Fungi against which medicines of the present invention may act effectively include, for example, fungi belonging to the genus *Aspergillus* such as *Aspergillus fumigatus, A. flavus, A. terreus* or *A. niger*; fungi belonging to the genus *Candida* such as *Candida albicans, C. tropicalis, C. kurusei* or *C. pseudotropicalis*; fungi belonging to the genus *Histoplasma* such as *Histoplasma capusulatum* or *H. fraciminosum*; fungi belonging to the genus *Microsporum* such as *Microsporum canis, M. distortum* or *M. nanam*; fungi belonging to the genus *Tricophyton* such as *Tricophyton gallinae, T. rubrum* or *T. equinum*; fungi belonging to the genus *Coccidioides* such as *Coccidioides immitis*; fungi belonging to the genus *Blastomyces* such as *Blastomyces dermatitis*; and fungi belonging to the genus *Cryptococcus* such as *Cryptococcus neoformans*. However, the present invention is not intended to be limited by the species of the fungi.

Parasites against which the medicines of the present invention may act effectively include, for example, malaria parasites such as *Plasmodium malariae, P. vivax, P. ovale, P. falciparum, P. knowlesi, P. cynomolgi, P. brasilianum* or *P. gallinaceum*. In addition, also included are *Histomonas tyzzer, Trypanosoma evavsi, T. hippicum, T. brucei, T. gambiense, T. cruzi, Leishmania donovani, L. tropoca, Trichomonas gallinae, T. gallinarum, T. hominis, T. foetus, T. vaginalis, Giardia intestinalis, G. duodenalis, G. canis, Entamoeba histolytica, Eimeria tenella, E. necatrix, E. maxima, E. acervulina, E. bruneetti, E. meleagrimitis, E. adenoeides, E. zurnii, E. ellipsoidalis, E. bovis, E. arloingi, E. parva, E. debliecki, E. spinosa, E. stiedae, E. perforans, E. magna, E. mustelae, E. vison, Isospora bigemina, I. felis, I. ribolta, Klossiella muris, Hepatocystes kochi, Haemoproteus columbae, Leucocytozoon simondi, L. caulleryi, Babesia bigemina, B. gibsoni, B. canis, B. caballi, B. equi, Theileria parva, T. annulata, T. buffeli, T. sergenti, Anaplasma marginale, Toxoplasma gondii, Encephalitozoon levaditi, Eperythrozoon wenyoni, Sarcocystis lindemanni, S. tenella, Plagiorchis muris, Dicrocoelium dendriticum, Eurytrema pancreaticum, Fasciola hepatica, F. gigantica, F. indica, Faciolopsis buski, Metrorchis orienntalis, M. akbidus, Microtrema truncatum, Centrocestus armatus, Echinostoma revolutum, Schistosoma japonicum, S. haematobium, S. mansoni, Diphyllobothunri latum, D. erinacei, Diplogonoporus grandis, Anoplocephala perforiata, A. magna, Bertiella studeri, B. mucronata, Helicometra giardi, Dipylidium canium, hymenolepsis nana, H. exigua, Raillietina cesticillus, R. kashiwarensis, Taenia solium, T. pisiformis, Taeniarhynchus saginatus, Multiceps multiceps, M. serialis, Echinococcus granulosus, E. multiocularis, Trichuris vulpis, T. suis, T. trichiura, Trichinella spiralis, Dioctophyma renale, Enterobius vermicularis, Ascaris lumbricoides, A. columnaris, Neoascaris vitulorum, Parascris equorum, Toxocara canis, T. cati, Anisakis genus, Strongylus equinus, S. edentatus, S. vulgaris, Anchlostoma caninium, A. tubaeforme, A. duodenale, Necator americanus, Burgia malayi, Dirofilaria immitis, D. aculiuscula, Setaria equina, S. digitata, S. servi* and *S. marshalli*. However, the present invention is not intended to be limited by the species of the parasites.

Viruses against which the medicines of the present invention may act effectively include, for example, viruses belonging to the pox virus family such as vaccinia virus, variola virus, monkeypox virus, yaba monkey tumor virus, cowpox virus, ectromelia virus, contagious pustular dermatitis virus, bovine papular stomatitis virus, fowlpox virus or human verruca virus; viruses belonging to the herpes virus family such as herpes simplex virus, variccela-zoster virus, human cytomegalovirus, malignant catarrhal fever virus, simian B virus, EB virus, pseudorabies virus, infectious bovine rhinotrancheitis virus, infectious avian Laryngotracheitis virus, Marek's disease virus, canine herpes virus, feline herpes virus, swine inclusion body rhinitis virus, carp pox virus or oncorhynchus masou virus; viruses belonging to the hepadonavirus family such as hepatitis B virus; viruses belonging to the adenovirus family such as human adenovirus, bovine adenovirus or simian adenovirus; viruses belonging to the papovavirus family such as human papilloma virus or JC virus; viruses belonging to the parvovirus family such as Aleutian mink disease virus, HB virus, feline panluekopenia virus or canine parvovirus; viruses belonging to the reovirus family such as Ibaraki virus, bluetongue virus, Colorado mite fever virus or rota virus; viruses belonging to the birnavirus family such as infectious bursal disease virus or infectious pancreatic nucreosis virus; viruses belonging to the orthomyxovirus family such as influenza A virus, fowl plaque virus or swine influenza virus; viruses belonging to the paramyxovirus family such as epidemic parotitis virus, mumpus virus, measles virus, Newcastle disease virus, parainfluenza virus, canine distemper virus or RS virus; viruses belonging to the rhabdovirus family such as rabies virus, vesicular stomatitis virus, bovine ephemeral fever virus, infectious hematopoietic necrosis virus or olivaceus (hirame) rhabdovirus; viruses belonging to the filovirus family such as Marburg virus or Ebola virus; viruses belonging to the coronavirus family such as human cold coronavirus, murine hepatitis virus, swine transmissible gastroenteritis virus, fowl infectious bronchitis virus, feline infectious peritonitis virus, equine arteritis virus or porcine reproductive respiratory syndrome virus; viruses belonging to the bunyavirus family such as hemorrhagic fever with renal syndrome virus, Akabane disease virus, Rift valley fever virus or California encephalitis virus; viruses belonging to the togavirus family such as equine encephalitis virus, Murray valley encephalitis virus, measles virus or equine arteritis virus; viruses belonging to the flavivirus family such as yellow fever virus, Japanese encephalitis virus or denguevirus; viruses belonging to the bunyamwera family such as Rift Valley fever virus or Akabane virus; viruses belonging to the retrovirus family such as avian leukemia virus, avian eticuloendotheliosis virus, feline leukemia virus, equine infectious anaemia virus, human spumavirus, human T-cell lymphotropic virus, human immunodeficiency virus or feline aquired immunodeficiency virus; viruses belonging to the iridovirus family such as lymphocele virus or sea beam iridovirus disease virus; viruses belonging to the picornavirus family such as human coxsakie virus, human echo virus, human polio virus, rhinovirus or foot-and-mouse disease virus; African swine fever virus; boma disease virus; and astrovirus. However, the present invention is not intended to be limited by the species of the viruses.

Medicines of the present invention may also act effectively against diseases caused by proteins such as bovine spongiform encephalopathy, transmissible mink spongiform encephalopathy, scrapie or Creutzfeldt-Jacob disease.

Mycoplasmas against which the medicines of the present invention may act effectively include, for example, mycoplasmas belonging to the genus *Mycoplasma*, such as *Mycoplasma mycoides*, *M. agalactiae*, *M. hyopneumoniae*, *M. capricolum*, *M. pulmonis* or *M. gallisepicum*. However, the present invention is not intended to be limited by them.

Rickettsias against which the medicines of the present invention may act effectively include, for example, rickettsias belonging to the genera *Rickettsia, Orientia, Coxiella, Ehrlichia, Wolbachia, Anaplasma, Haemobartonella, Eperythrozoon* and *Bartonella*.

*Chlamydia* against which the medicines of the present invention may act effectively include, for example, *Chlamydia trachomatis, C. pneumoniae, C. psittaci* or *C. pecorum*.

In the present invention, however, the microorganisms are not limited to those mentioned above.

Medicines according to the present invention which comprise reduced riboflavin and/or a reduced riboflavin derivative or pharmacologically acceptable salt thereof as active ingredient may have a potent immunomodulating effect.

The diseases on which administration of medicines according to the present invention comprising reduced riboflavin and/or a reduced riboflavin derivative or pharmacologically acceptable salt thereof as active ingredient may be effective include infectious diseases by the microorganisms mentioned above. The inventive medicines may have excellent effects on the infectious diseases as an immunostimulator and infection-protective/treating medicine. The medicine may also be highly effective for preventing or treating malignant tumors, hematological disorders, hepatic. diseases, collagen disease, renal metabolic diseases and infections before and after operation.

The inventive medicines may also be effective on systemic inflammatory response syndrome (SIRS) caused by the systemic microbial infection and has a remarkable effect as a preventive/treating medicine for sepsis. Further, the inventive medicines may have extremely excellent effects as a preventive/treating medicine for septic shock and a preventive/treating medicine for toxin shock. They may also have an effect as a preventive/treating medicines for disseminate intravascular coagulation (DIC), multiple organ failure (MOF) and/or adult respiratory distress syndrome (ARDS).

The inventive medicines may also have an excellent effect as a preventive/treating medicine for malarial diseases.

The inventive medicines may act. effectively on diseases. on which immunomodulating action is-effective, such as autoimmune diseases (e.g., chronic rheumatoid arthritis, multiple sclerosis, amyotrophic lateral sclerosis, systemic lupus erythematosus, Behcet's disease, idiopathic thrombocytopenic purpura, myasthenia gravis, nodular arteriosclerosis, ulcerative colitis, Crohn's disease, atopic dermatitis and pollinosis), ischaemia-referfusion injuries (e.g., cerebral infarction and myocardial infarction), hemorrhagic shock, photosensitive dermatitis, empyema, pyometra, otitis media, peritonitis, infectious endocarditis, diarrhea and dementia.

EXEMPLIFICATION

The present invention will be illustrated by the following examples, but is not intended to be limited by these examples.

Example 1

Effect on *E. coli*-Infected Model

Twelve mg of riboflavin sodium phosphate (FMN-Na, JP grade) was dissolved in 40 ml of physiological saline and then added and mixed with 480 mg of sodium hydrosulfite to produce leucoflavin phosphate (FMN-$H_2$).

Male mice (Slc: ICR, 8-week old) (10 mice per each test group) was administered intraperitoneally with each of riboflavin sodium phosphate (dosage: 12.5, 25, 50 and 100 mg/kg in dosage volumes of 0.125, 0.25, 0.5 and 1 ml, respectively) and leucoflavin phosphate (dosage: 1.25, 2.5, 5 and 10 mg/kg in dosage volumes of 0.125, 0.25, 0.5 and 1 ml, respectively) which had been dissolved in physiological saline and sterilized by filtration. Twenty-four hours after the administration, *E. coli* E01292 strain was inoculated subcutaneously at a dose of $5.3 \times 10^7$ CFU/mouse (suspended in 0.2 ml of physiological saline), and the survival rate was determined 4 days after the inoculation. In the control group, 1.0 ml of physiological saline was administered intraperitoneally instead of the drugs. The determination of the medicinal efficacy was conducted by $\chi^2$ test. The results are shown in Table 1.

TABLE 1

| Test group | Survival rate survival number (survival rate %) |
|---|---|
| Control | 0 (0) |
| VB$_2$Na 12.5 mg/kg | 1 (10) |
| VB$_2$Na 25 mg/kg | 3 (30) |
| VB$_2$Na 50 mg/kg | 5 (50)* |
| VB$_2$Na 100 mg/kg | 9 (90)** |
| FMN-H$_2$ 1.25 mg/kg | 0 (10) |
| FMN-H$_2$ 2.5 mg/kg | 4 (40) |
| FMN-H$_2$ 5 mg/kg | 6 (60)** |
| FMN-H$_2$ 10 mg/kg | 9 (90)** |

VB$_2$Na: riboflavin sodium phosphate
FMN-H$_2$: leucoflavin phosphate
*: $P < 0.05$,
**: $P < 0.01$ As shown in Table 1, leucoflavin phosphate showed about 10-fold greater infection-protective effect against *E. coli* compared with riboflavin sodium phosphate.

Example 2

Effect on *Staphylocuccus aureus*-Infected Model

Riboflavin sodium phosphate (FMN-Na, JP grade) and leucoflavin sodium phosphate (FMN-H$_2$) prepared in Example 1 were used.

Male mice (Slc: ICR, 8-week old) (10 mice per each test group) was administered intraperitoneally with each of riboflavin sodium phosphate (dosage: 25, 50 and 100 mg/kg in dosage volumes of 0.25, 0.5 and 1 ml, respectively) and leucoflavin phosphate (dosage: 2.5, 5 and 10 mg/kg in dosage volumes of 0.25, 0.5 and 1 ml, respectively) which had been dissolved in physiological saline and sterilized by filtration. Twenty-four hours after the administration, *Staphylococcus aureus* BO-72 strain was administered intravenously at a dose of 8.7×10$^7$ CFU/mouse (suspended in 0.2 ml of physiological saline), and the survival rate was determined 10 days after the inoculation. In the control group, 1.0 ml of physiological saline was administered intraperitoneally instead of the drugs. The determination of the medicinal efficacy was conducted by $\chi^2$ test. The results are shown in Table 2.

TABLE 2

| Test group | Survival rate survival number (survival rate %) |
|---|---|
| Control | 0 (0) |
| VB$_2$Na 25 mg/kg | 2 (20) |
| VB$_2$Na 50 mg/kg | 4 (40) |
| VB$_2$Na 100 mg/kg | 7 (70)** |
| FMN-H$_2$ 2.5 mg/kg | 3 (30) |
| FMN-H$_2$ 5 mg/kg | 6 (60)** |
| FMN-H$_2$ 10 mg/kg | 8 (80)** |

VB$_2$Na: riboflavin sodium phosphate
FMN-H$_2$: leucoflavin phosphate
*:P < 0.05,
**:P < 0.01

As shown in Table 2, leucoflavin phosphate showed about 10-fold greater infection-protective effect against *Staphylococcus aureus* compared with riboflavin sodium phosphate.

Example 3

Effect on Endotoxin Shock Model

Riboflavin sodium phosphate (FMN-Na, JP grade) and leucoflavin sodium phosphate (FMN-H$_2$) prepared in Example 1 were used.

Male mice (Slc: ICR, 6-week old) (10 mice per each test group) was administered intraperitoneally with lipopolysaccharide from *E. coli* serum type 0111-B4 (Sigma; abbreviated as "LPS" hereinbelow) at a dose of 15 mg/kg.

Six hours after the administration, each of riboflavin sodium phosphate (dosage: 5, and 20 mg/kg in dosage volumes of 0.25, 0.5 and 1 ml, respectively) and leucoflavin phosphate (dosage: 2.5, 5 and 10 mg/kg in dosage volumes of 0.25, 0.5 and 1 ml, respectively) which had been dissolved in physiological saline and sterilized by filtration was administered intraperitoneally. The survival rate was determined 4 days after the administration. In the control group, 1.0 ml of physiological saline was administered intraperitoneally instead of the drugs. The determination of the medicinal efficacy was conducted by $\chi^2$ test. The results are shown in Table 3.

TABLE 3

| Test group | Survival rate survival number (survival rate %) |
|---|---|
| Control | 0 (0) |
| VB$_2$Na 5 mg/kg | 3 (30) |
| VB$_2$Na 10 mg/kg | 4 (40) |
| VB$_2$Na 20 mg/kg | 7 (70)** |
| FMN-H$_2$ 2.5 mg/kg | 2 (20) |
| FMN-H$_2$ 5 mg/kg | 6 (60)** |
| FMN-H$_2$ 10 mg/kg | 8 (80)** |

VB$_2$Na: riboflavin sodium phosphate
FMN-H$_2$: leucoflavin phosphate
*:P < 0.05,
**:P < 0.01

As shown in Table 3, leucoflavin phosphate showed about 2-fold greater life-saving effect on endotoxin shock than riboflavin sodium phosphate.

The invention claimed is:

1. A method for treating sepsis, comprising administering a pharmacologically effective amount of a reduced riboflavin and/or a reduced riboflavin derivative or pharmacologically acceptable salt thereof to a subject in need thereof, wherein the reduced riboflavin is selected from the group consisting of leucoflavin and pharmaceutically acceptable salts thereof, and wherein the reduced riboflavin derivative is selected from the group consisting of leucoflavin mononucleotide, leucoflavin adenine dinucleotide and pharmaceutically acceptable salts thereof.

2. The method according to claim 1, wherein the pharmaceutically acceptable salt of leucoflavin is leucoflavin phosphate ester.

* * * * *